United States Patent [19]

Blott

[11] Patent Number: 5,380,260

[45] Date of Patent: Jan. 10, 1995

[54] MEDICAL PADDINGS

[75] Inventor: Patrick L. Blott, Bishops Stortford, United Kingdom

[73] Assignee: Smith & Nephew plc, England

[21] Appl. No.: 150,236

[22] Filed: Nov. 9, 1993

Related U.S. Application Data

[63] Continuation of Ser. No. 773,655, Oct. 15, 1991, abandoned.

[30] Foreign Application Priority Data

Aug. 15, 1989 [GB] United Kingdom ............... 8918572

[51] Int. Cl.⁶ .............................................. A61F 13/00
[52] U.S. Cl. ........................................ 602/41; 602/45
[58] Field of Search ............... 602/2, 5, 6, 7, 8, 9, 602/12, 13, 41, 60–66

[56] References Cited

U.S. PATENT DOCUMENTS

| | | | |
|---|---|---|---|
| 3,421,501 | 1/1969 | Beightol | 602/8 |
| 3,944,688 | 3/1976 | Inman . | |
| 4,019,506 | 4/1977 | Eschmann | 602/8 |
| 4,062,818 | 12/1977 | Mate . | |
| 4,235,228 | 11/1980 | Gaylord | 602/8 |
| 4,294,240 | 10/1981 | Thill . | |
| 4,320,750 | 3/1982 | Dabroski | 602/8 |
| 4,411,928 | 11/1983 | Baldwin . | |
| 4,516,572 | 5/1985 | Schlein . | |
| 4,655,202 | 4/1987 | Potter | 602/8 |
| 4,745,912 | 5/1988 | McMurray | 602/8 |
| 4,989,593 | 2/1991 | Carpagna | 602/8 |
| 5,027,803 | 7/1991 | Scholz | 602/8 |

FOREIGN PATENT DOCUMENTS

| | | |
|---|---|---|
| 0061642 | 3/1982 | European Pat. Off. . |
| 0352094 | 7/1989 | European Pat. Off. . |
| 105450 | 7/1980 | Japan . |
| 105451 | 7/1980 | Japan . |
| 135756 | 7/1983 | Japan . |
| 1336214 | 3/1970 | United Kingdom . |
| 1335123 | 3/1971 | United Kingdom . |
| 2038639 | 12/1979 | United Kingdom . |
| 2055582 | 7/1980 | United Kingdom . |
| 2203945 | 12/1987 | United Kingdom . |
| 2200286 | 1/1988 | United Kingdom . |

Primary Examiner—Michael A. Brown
Attorney, Agent, or Firm—Rosenman & Colin

[57] ABSTRACT

A moisture vapor permeable, water impervious padding including sheets or strips of a lofted non-woven fabric having wax, silicone resin or fluorinated polymer at a surface layer thereof. The sheet or strip may be formed into a tube and contain an elastic component in the circumference to result in an elastically extensible tubular undercast padding.

24 Claims, 1 Drawing Sheet

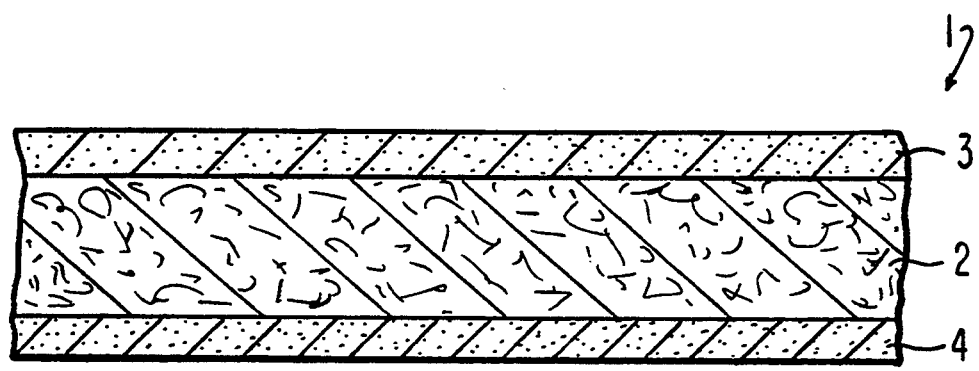

MEDICAL PADDINGS

This application is a continuation of 07/773,655, file Oct. 15, 1991, now abandoned.

The present invention relates to medical paddings for orthopaedic use and in combination with an orthopaedic cast material and to methods for the preparation thereof.

Treatment of bone deformities of the body such as bone fractures usually involves immobilisation of a portion of the body. The immobilisation of the body portion is commonly provided by a rigid cast made of plaster of Paris or a plastics material. Such rigid casts normally remain on the body for one to two months and as a result often cause trauma and discomfort to the patient. Trauma can De caused by chaffing at those parts of the body, for example protuberances, which are placed under pressure by the cast. Such chaffing and may lead to ulceration of the skin and tissue overlying a protuberance. Trauma and discomfort such as skin itching and maceration can also be caused by moisture trapped under the cast. Such moisture may be provided by skin perspiration under the cast, water from a wet cast during the setting thereof or water contacting the cast during wear for example during washing. To alleviate these problems it is now normal to apply a medical padding to the body portion prior to forming the cast to provide a cushion between the cast and the body. The medical padding commonly used for this purpose is a sheet or strip of fibrous wadding which can be wrapped around the body portion either alone or together with a tubular knitted or woven stockinette which can conveniently be applied over a body extremity onto the body portion. Paddings in the form of a wadding made of hydrophilic fibres such as cotton fibres are well known in the art. Such paddings can advantageously absorb perspiration from the skin. These paddings however can also absorb water from other sources which may occur during the preparation and/or wearing of the cast and therefore in use are likely to maintain the surface of the skin adjacent thereto in an undesirable moist environment. Paddings in the form of a wadding made of hydrophobic fibres such as polypropylene or polyester fibres are also known in the art. A known padding of this type which comprises polyester fibres is known as SOFFBAN Orthopaedic Padding marketed by Smith & Nephew. It has been found, however, that in use waddings made of hydrophobic fibres although relatively non-absorbent do allow transmission of water to the skin surface where it can be trapped until it drains or evaporates from the wadding. Such waddings have also been found to be uncomfortable to wear under a cast. A medical padding has now been found which has considerable advantages over prior art medical paddings and comprises a water vapour permeable, water impervious sheet or strip of lofted non-woven fabric.

Thus in accordance with the present invention there is provided a moisture vapour permeable water impervious sheet or strip of medical padding for orthopaedic use which comprises lofted non-woven fabric comprising synthetic fibres and which has wax at a surface layer of the fabric.

The present invention further provides a elastically extensible, tubular, moisture vapour permeable, water impervious medical padding for orthopaedic use comprising a sheet or strip of lofted non-woven fabric which has wax, silicone resin or fluorinated polymer at a surface layer of the fabric and circumferentially arranged elastic component.

BRIEF DESCRIPTION OF THE DRAWINGS

The Figure is an elevational view, in section, of a medical padding according to the invention.

DETAILED DESCRIPTION

Referring to the Figure, one embodiment of the invention is the medical padding strip 1 composed of a lofted non-woven fabric 2 impregnated with wax 3, 4 at the opposed surfaces thereof, such as described in Example 1 hereinbelow.

A lofted non-woven fabric as used herein is a non-woven fibre fabric of sufficient thickness for single layer to provide a cushion for an immobilising rigid cast on a portion of the body. The non-woven fabric used in the invention can aptly have a thickness of in excess of 2 mm. Suitably the thickness of the fabric can be upto 10 mm and may generally be in the range of from 2 to 10 mm and preferably have a thickness of 3 to 8 mm typically about 5 mm. Similarly the non-woven fabric can aptly have a weight per unit area of greater than 5 $gm/m^2$. The weight of the fabric in most cases need not exceed 200 $gm/m^2$ and suitably will be in the range of from 5 to 200 $gm/m^2$ depending on the nature of the fibre. Preferably the weight of fabric comprising natural fibres will be in the range of from 75 to 150 $g/m^2$ whereas for fabrics comprising synthetic films the weight of the fabric will be preferably from 5 to 20 $g/m^2$.

The lofted non-woven fabric will preferably be formed in a manner to render the fabric resilient.

Such a lofted non-woven fabric can be a wadding of natural or synthetic fibres of the type conventionally used as medical paddings.

The lofted non-woven fabric of the invention, is both water vapour permeable to allow the escape of moisture from under the cast and water impervious to inhibit exterior water penetrating through the padding to the surface of the skin.

The paddings of the invention are water impervious to the extent that when water is placed on a surface of the padding it will remain on the surface, and can be rolled off rather than penetrate the surface of the padding.

The non-woven fabric used in the paddings of the invention may be rendered water impervious by treatment with certain waterproofing or water repelling agents.

Suitable waterproofing agents include non-toxic waterproofing agents used for textiles such as wax, silicone resin or fluorinated polymer waterproofing agent. Such an agent are normally available as a solution or dispersion.

Medical paddings comprising fabrics which have a wax at a surface layer are especially preferred. It is believed that, with such paddings, whilst the initial water repelling properties are at least as good as paddings comprising fabrics having a silicone resin or fluorinated polymer at said surface, the water shedding properties of the "waxed" paddings are, surprisingly, superior to that of the silicone resin and fluorinated polymer treated paddings.

For strip or sheet paddings the fabric has a wax at a surface layer thereof. For tubular paddings the fabric may have a silicone resin or fluorinated polymer at a surface layer thereof although wax is preferred.

The waxes employed in the present invention include hydrocarbon based materials such as paraffin waxes for example. Aptly the waxes are employed in emulsion form such as wax-metal emulsions. Suitable wax-metal emulsions include dispersions containing aluminium or zirconium salts such as 'Super-pel', a dispersion of paraffin waxes in zirconyl acetate solution containing about 17% by weight wax, obtainable from Grangers Ltd, Watford, U.K. When applied to the fabric or fabric layers the dispersion may be further diluted for example to 5% w/v in water. Another wax emulsion available for use in the invention is NICKWAX TX10 available from Nickwax Ltd.

Apt waxes for use with polyester fibre non-woven fabrics are a wax waterproofing agents in emulsion form known as Nickwax TX10 available from Nickwax Ltd. and Super pel available from Grangers Ltd.

Apt silicone resins for use in the paddings of the present invention include any of the known silicones which provide water repellency. Suitable materials include those based on polymers of methyl (hydrogen) siloxane and of dimethysiloxane. Such silicon resins may be supplied as aqueous emulsions or solvent solutions typically at silicone solids content of from 0.5 to 8%. Suitable materials include silicone emulsions sold under the designation BC84/85 by Basildon Chemicals and silicone solutions sold under the designation WR50 by Basildon Chemicals. Other suitable silicone resins for use in the present invention include silicones supplied by Dow Corning Corporation, Union Carbide Corporation and the General Electric Corporation. A suitable Dow-Corning silicone resin is that designated C2-0563.

The fluorinated polymers employed in the present invention may be any of those known for providing repellency to water. Preferred materials are those manufactured and marketed by Minnesota Mining and Manufacturing Company under the trade name 'Scotchguard' Other suitable fluoropolymers include emulsions sold under the designation 'HansaPhob 6801' by Hansa Textile Chemicals.

The non-woven fabric may be treated, for example by coating, to provide the waterproof agent at a surface layer of the fabric. Alternatively the agent may be provided throughout the thickness of the fabric, as well as at the surface, by, for example impregnation by the agent.

Moisture vapour permeable non-woven fabrics used in the invention can suitably have a moisture vapour transmission rate of at least 1000 g/m$^2$/24 h, more suitably at least 2000 g/m$^2$/24 h and preferably at least 5000 g/m$^2$/24 h at 37° C. at 100% to 10% relative humidity difference. The moisture vapour transmission rate of a non-woven fabric can be readily determined by the Payne Cup Method (in the upright position) described in European Patent No. 46071.

The lofted non-woven fabric used in the paddings of the invention can be a wadding of natural or synthetic fibres. Such a wadding can comprise hydrophilic fibres or hydrophobic fibres or blends thereof.

Suitable hydrophilic fibres for use with tubular paddings include cellulosic fibres such as cotton and viscose rayon fibres. Hydrophilic fibres can advantageously provide the lofted non-woven fabric with softness to skin and the capacity to absorb perspiration.

Suitable hydrophobic fibres for use with both strip or sheet and tubular paddings include polyester, polypropylene and high density polyethylene fibres. Hydrophobic fibres render the lofted non-woven fabric relatively non-absorbent so that water penetrating the fabric can drain away.

The lofted non-woven fabric can also comprise meltable fibres such as conjugated or bicomponent fibres of higher and lower melting points to bond the fibres in the fabric.

An apt resilient lofted non-woven fabric for use in the tubular paddings of the invention which comprises hydrophilic fibres is known as SOFFBAN natural orthopaedic padding available from Smith & Nephew. Such a non-woven fabric comprises viscose rayon fibres, has a thickness of 3.6 to 4.2 mm and a weight per unit area of 105 to 140 g/m$^2$.

An apt resilient lofted non-woven fabric for use in the invention which comprises hydrophobic fibres is known as SOFFBAN synthetic orthopaedic padding available from Smith & Nephew. Such a non-woven fabric comprises a blend of polyester fibres (85%) and meltable conjugate fibres (15%) having a polypropylene core surrounded by a high-density polyethylene layer, has a thickness of 4.25 to 5.25 mm and a weight per unit area 7.5 to 10 g/m$^2$.

Lofted non-woven fabrics which comprise hydrophobic fibres are relatively non absorbent and also tend to feel rough against the skin. Such a lofted non-woven fabric strap or sheet used in the invention preferably comprises a body facing layer of a soft liquid pervious fabric comprising hydrophobic or hydrophilic fibres to render the fabric absorbent or permeable to perspiration and soft against the skin. Such a body facing layer can be favourably be non-woven fabric, woven or knitted fabric of cellulosic fibres. This body facing layer, however, is preferably thinner than the main portion of the lofted non-woven fabric.

In one embodiment of the invention the medical padding is in the form of a sheet or preferably a strip. Such a sheet or strip can be applied to a patient by wrapping or winding the sheet or strip about a portion of the body to which the cast will be applied. The size of sheet or strip can be adapted to the size of the body portion to which it is to be applied. The medical padding, however, may be in the form of larger roll from which a suitable length may be cut or preferably torn. In preferred embodiments the sheet or strip is tearable.

In another embodiment of the invention the medical padding is in the form of a tube which comprises a strip or sheet of the lofted non-woven fabric used in the invention.

Such a tube can comprise a strip of the non-woven fabric in a spirally wound form or a sheet of the non-woven fabric joined at opposed edges thereof. Alternatively, the tubular padding may comprise two or more strips of the Lofted non-woven fabric arranged in parallel to form the circumference of a tube. The longitudinal edges of the strip may be bonded together to form the tube.

A medical padding tube will usually be applied to the patient by passing the tube over a body extremity to the body portion to which the cast is to be applied, Preferably the medical padding tube comprises an elastic component or components in its circumference to render the tube elastically expandable. Such a tube of suitable size can advantageously accommodate a body extremity during its passage thereover and also conform to body portion to which it is applied.

Suitable elastic components include elastic yarns conventionally used in elastic fabrics such as rubber or polyurethane threads or strips.

The elastic component or components in an elastic tubular medical padding can conveniently extend in a circular spiral fashion around the circumference of the tube.

In favoured embodiments of this type the tubular strip or sheet of lofted non-woven fabric is an outer layer which is attached to an inner tubular layer of a soft fabric as hereinbefore described. Such a tubular soft fabric can conveniently be a knitted stockinette or a woven or a non-woven fabric tube. The elastic component for example a rubber thread can form part of the soft fabric or be located between the outer and inner layers of the tube.

In a preferred form of this embodiment one or more for example two strips of non-woven fabric may be laid down and attached to the tubular inner extendible layer such that the longer sides of the strips are co-axial with the major axis of the inner layer. The adjacent edges of the non-woven fabric may be joined to form an annular cylinder around the inner tubular layer. Alternatively, the edges of the non-woven fabric need not be attached to each other. The non-woven fabric will be in the form of a segmented cylinder around the inner tubular layer.

The outer and inner layers can suitably be attached by any conventionally heat or adhesive bonding or by a mechanical method such as stitching.

The inner and outer layers of the medical padding tube are preferably attached by a moisture vapour permeable layer pressure sensitive adhesive. A continuous layer of such an adhesive will advantageously also be water impervious.

Favoured moisture vapour permeable adhesives for this purpose are the polyvinyl ether and acrylate ester adhesives disclosed in United Kingdom Patent Nos. 128063 and 2070631. An apt adhesive is a pressure sensitive adhesive copolymer of 47 parts by weight of n-butyl acrylate, 47 parts by weight of 2-ethyl hexyl acrylate and 6 parts by weight of acrylic acid made according to method disclosed in United Kingdom Patent No. 2070631.

The outer and inner layers can be heat bonded by means of a hot melt adhesive or interposed heat meltable layer.

In an elastic tubular medical padding the non-extensible layers in the wall of the tube will normally be in an undulating folded form in at least in the circumferentially direction thereof to render the layers extensible in that direction. The wall of the will therefore usually exhibit a substantially longitudinal crepe, crinkled or folded pattern. Such underlating folds of a lofted non-woven fabric layer advantageously increases the thickness of the layer.

As hereinbefore described the medical padding of the invention can be used to provide a cushion for the immobilised body portion under a cast.

In another aspect the present invention provides a medical padding of the invention in combination with a orthopaedic cast material.

In a further aspect the present invention provides a method forming a moisture vapour permeable water impervious elastic tubular material padding of the invention which comprises attaching an outer layer of a strip or sheet of lofted non-woven fabric to an inner layer of tubular elastic fabric.

The outer layer of non-woven fabric strip or sheet used in the process of the invention can be rendered impervious prior to being attached to the inner layer by a suitable waterproof agent or a suitable coating of a water vapour permeable, water impervious polymer layer as hereinbefore described.

A waterproof agent as a dispersion can be coated, sprayed or impregnated into the non-woven fabric by a conventional method.

Suitable water vapour permeable, water impervious polymer layer can be coated as melt, solution or dispersion onto the non-woven fabric or onto a substrate which may be a release substrate for bonding for example by heat sealing onto the non-woven fabric.

In the process of the invention the lofted non-woven fabric layer can be provided with undulating folds to render the layer extensible prior to, during or after it attached to inner layer of tubular elastic fabric.

Prior to attachment the lofted non-woven fabric layer can be embossed or compressed to provide the undulating folds. The undulating folds in the layer can also be provided by bonding, for example by adhesive or heat bonding the layer in a folded form to discrete linear areas of the inner layer. In a preferred process of the invention the outer layer of lofted non-woven fabric is attached to an expanded inner layer of tubular elastic fabric and the composite layered tub is allowed to contract. In such a process the composite tube are provided with an undulating folds in the circumferentially direction thereof.

The tubular fabric used in the process can conveniently be expanded over a mandrel of suitable size. The tubular fabric can be an elastic fabric for example a woven fabric which comprises an elastic thread in its circumference. Alternatively the tubular fabric can be a tubular knitted fabric or a non woven fabric strip or sheet which has been formed into a tube which has been rendered elastic by attaching tensioned elastic thread or threads in a circular or spiral fashion around the outside of the inner layer.

In a preferred process of the invention the outer surface of the inner layer of tubular fabric is provided with adhesive and the elastic component or components such as a thread if required and the outer layer of lofted non-woven fabric strip or sheet is attached to inner layer by the adhesive. The adhesive can be provided prior or after expansion of the tubular fabric by any convenient method for example transfer coating method.

When the tubular fabric inner layer is expanded on a rotatable such as a driven rotatable mandrel, the adhesive, elastic and non-woven fabric components in thread or strip form can conveniently be applied around the inner layer -while the mandrel is rotating. The tension in an elastic thread which is spirally wound around such a rotating mandrel can be adjusted by controlling the speed at which the elastic thread is fed into the mandrel.

The expanded composite layered padding can then be removed from the mandrel and allowed to contract.

The medical paddings of the present invention may be employed in combination with a body immobilising cast.

Therefore in accordance with a further aspect of the present invention there is provided, in combination a body immobilising cast and a medical padding of the invention.

Although the medical paddings of the invention may be employed with any known casting materials including plaster of Paris particularly suitable casting or splinting materials for use with the paddings of the invention are synthetic resin based casting or splinting systems such as those based on polyurethane resins.

Such casting materials are available as a resin impregnated bandaging substrate, for example, polypropylene or glass fibre substrates. Once wetted with water the resin will cure and set.

Suitable polyurethane splinting resins and systems which may be used in combination with the paddings of the present invention include those described in U.S. Pat. Nos. 4427002 and 4574793.

In a further aspect of the present invention there is also provided a method of immobilising a body portion which comprises first applying a medical padding in accordance with the invention and thereafter applying an immobilising cast, for example applying the casting or splinting materials and systems described above.

The invention will now be illustrated by reference to the following examples.

Example 1

A medical padding strip of the invention was prepared by immersing a strip (length 3 m, width 80 mm) of conventional orthopaedic padding into bucket of water containing a waterproofing agent (Nickwax TX10 dispersion at a 1:3 dilution) until fully impregnated, withdrawing the strip and allowing excess liquid to be off and then drying the strip in an oven at 80° C.

The padding used in this example was a lofted non-woven fabric (weight per unit 8.5 $g/m^2$, thickness approximately 5 mm) of heat bonded polyester fibres.

It was found in a test that water placed on tilted surface of the waterproofed padding of the invention tended to roll off whereas water similarly placed onto a tilted surface of the conventional padding immediately penetrated through the padding to the other surface.

Example 2

An elastic tubular medical padding of the invention was prepared by mounting a conventional tubular knitted cotton stockinette in expanded state over mandrel (diameter 204 mm) connected to motor. An adhesive layer (25 $g/m^2$) was transfer coated from silicone release paper onto the outer surface of stockinette and tensioned elastic rubber thread spirally wound (space between turns 2 cm) onto the adhesive surface of the stockinette.

The adhesive used was a pressure sensitive adhesive copolymer of 47 parts by weight n-butyl acrylate 47 parts by weight of ethyl hexyl acrylate and 6 parts by weight of acrylic acid. The tension of elastic thread was obtained by feeding the thread from a roll which was driven at a lower surface speed than that of the mandrel. A strip (width 60 mm) of waterproofed padding material similar to that of Example 1 was then spirally wound over the elastic thread and the adhesive surface of the stockinette. The expanded tube was then removed from the mandrel and allowed to elastically retract to form crinkled walls. The tubular padding had a length of 29 cm and a diameter of approximately 6.4 cm which could be elastically expanded to a diameter of 14.6 cm.

Example 3

A medical padding was formed in the same manner as Example 2 except that an inner tube of spirally wound non-woven fabric (Spun bonded polyester fibres available from Asahai) was used in place of the stockinette. The medical padding had length of 20 cm and diameter of 5.7 cm which could be expanded to diameter of 12.1 cm.

Example 4

A sample of SOFFBAN synthetic orthopaedic padding was impregnated with a paraffin wax composition by passing a 15 cm wide strip of the padding, delivered from a roll through an aqueous impregnation bath containing 5% weight/volume of Super Pel maintained at a temperature of 50° C. The padding was drawn through the bath at a rate of 1.8 m/min and thereafter passed through a nip to remove excess bath solution. After passage through the bath the impregnated padding was passed through a washing bath of warm water at a temperature of 50° C. and at a rate of 1.8 m/min. After washing the impregnated padding was dried for 1 hour at a temperature of 80° C.

Example 5

A tubular undercast padding was prepared by first coating a hot melt adhesive (Lunatac 534 HBI) onto a release coated paper at an adhesive coating weight of 43 grams per square meter. The adhesive was transfer coated onto an unstretched sample of elasticated stockinette using a hot iron.

The coated stockinette was then stretched on a board for a width of 7.5 cm to 21 cm. Stretching of the stockinette caused the adhesive to fragment and thus form a dicontinuous coating.

The adhesive was activated by blow air heated to a temperature of 150° C. onto the coated stockinette and thereafter 15 cm strips of treated SOFFBAN were laid down in parallel onto the activated adhesive surface to form a tubular composite elastically extensible undercast padding.

The treated SOFFBAN material was produced in one of three ways:

1. A wax treated SOFFBAN padding was produced in accordance with the procedure described in Example 4.

2. Silicone Resin

A SOFFBAN synthetic padding was employed and the procedures of Example 4 was adopted except that the impregnation bath consisted of 6% w/v solution in water of a silicone emulsion designate BC 84/84, available from Basildon Chemicals. The impregnated padding was not rinsed with water but dried and cured at 120° C. for 2 minutes in a hot air oven immediately after the removal of excess bath solution.

3. Fluorinated Polymer

The procedure of Example 3 was adopted except that the impregnation bath consisted of 2% weight by volume a fluropolymer designated Hanse Phob 6801 (available from Hansa Textile Chemicals), acidified by the addition of 0.2% weight by volume of acetic acid. The impregnated padding, after removal of excess bath solution was passed directly to the drying stage where it was cured at 150° C. for 3 minutes in hot air.

Samples of the treated composite undercast padding were then tested for their water repellency properties in the following manner. A 'syringe' comprises two cylinders; an inner one fitting closely within an outer cylinder. The inner cylinder has an internal diameter of 38 mm. Across the lower end of the inner cylinder a sample of the padding is affixed. A hydrostatic head test is performed by immersing the lower ends of both cylinders in a bath of water at 20° C. with the lower end of the outer cylinder near the bottom of the bath and the lower end of the upper cylinder near the surface. The inner cylinder is then pushed downwards at a rate of 20 mm/min until water penetrates through the substrate. The distance (depth) moved by the substrate is measured and records as $H^1$ mm. The values for $H_1$ give an indicator of the resistance to water penetration. The greater the value for $H_1$ the greater the resistant to penetration.

In a second test, the lower ends of both cylinders are just below the surface of the bath. The inner cylinder is then drawn upwards until air bursts through the sample and the column of water formed thus far drops. The height or distance moved by the substrate to the point where air breaks through is measured and records as $H^2$. The value for $H_2$ gives an indicator of the ability of the padding to shed water. The lower the value of $H_2$ the better will be the water shedding properties of the padding.

Both hydrostatic heads tests were carried out on samples treated with wax, silicone resin, fluorinated polymer and a control in which the SOFFBAN had not been treated and the results for $H_1$ and $H_2$ are reported in the following table:

| Material | $H_1$ (mm) | $H_2$ (mm) |
| --- | --- | --- |
| Wax | 48.9 | 23.9 |
| Silicone | 32.9 | 27.5 |
| Fluoropolymer | 50.5 | 38.8 |
| Control | 14.1 | 38.2 |

From the results it will be noted that the wax treated padding shows similar properties to fluropolymer treated material in regard to initial water repellency ($H_1$) and is superior with respect to both the silicone and fluoropolymer treated materials in respect of its water shedding properties.

I claim:

1. A moisture vapour permeable water impervious sheet or strip of medical padding for orthopaedic use which comprises lofted non-woven fabric comprising synthetic fibres and which has wax at a surface layer of the fabric.

2. A padding as claimed in claim 1 wherein the wax is impregnated throughout the surface of the fabric.

3. A padding as claimed in claim 1 wherein the fabric comprises hydrophobic synthetic fibres.

4. A padding as claimed in claim 3 wherein the fabric comprises polyester or polypropylene fibres.

5. A padding as claimed in claim 1 wherein the fabric has a thickness of from 2 to 10 mm.

6. A padding as claimed in claim 1 having a moisture vapour permeability of at least 1000 $g/m^2/24$ h at 37° C. at a 100% to 10% relative humidity difference.

7. In combination, a body immobilising cast and a padding as claimed in claim 1.

8. A method for immobilising a body portion which comprises applying a padding as claimed in claim 1 and thereafter applying a body portion immobilising cast.

9. A elastically extensible, tubular, moisture vapour permeable, water impervious medical padding for orthopaedic use comprising a sheet or strip of lofted non-woven fabric which has wax, silicone resin or fluorinated polymer at a surface layer of the fabric and a circumferentially arranged elastic component.

10. A padding as claimed in claim 9 wherein the wax, silicone resin or fluorinated polymer is impregnated throughout the fabric.

11. A padding as claimed in claim 5 wherein the fabric has a wax at a surface layer thereof.

12. A padding as claimed in claim 9 wherein the fabric comprises hydrophilic fibres.

13. A padding as claimed in claim 12 wherein the fibres are natural fibres.

14. A padding as claimed in claim 9 wherein the fibres are synthetic fibres.

15. A padding as claimed in claim 14 wherein the fabric comprises hydrophobic fibres.

16. A padding as claimed in claim 9 wherein the elastic component comprises an elastic yarn.

17. A padding as claimed in claim 9 in which a strip of fabric is spirally wound to form a tube.

18. A padding as claimed in claim 9 in which the fabric is attached to an inner tubular fabric layer.

19. A padding as claimed in claim 18 wherein the inner tubular layer is a knitted, woven or non-woven fabric.

20. A padding as claimed 18 wherein the inner tubular layer comprises an elastic component.

21. A padding as claimed in claim 20 wherein the elastic component is a yarn, thread of strip comprising an elastomer.

22. A padding as claimed in claim 18 wherein the fabric sheet or strip is heat bonded, adhesively bonded or mechanically bonded to the inner tubular layer.

23. A padding as claimed in claim 22 wherein the fabric is bonded to the inner tubular layer by a moisture vapour permeable layer of a pressure sensitive adhesive.

24. A padding as claimed in claim 9 comprising circumferentially arranged folds of a layer of non-extensible lofted non-woven fabric attached to an inner elastically extensible tubular layer of a knitted, woven or non-woven fabric.

* * * * *